US008440190B2

(12) United States Patent
Waldmann et al.

(10) Patent No.: US 8,440,190 B2
(45) Date of Patent: May 14, 2013

(54) ANTIBODY VARIANTS (75) Inventors: Herman Waldmann, Oxford (GB); Lisa K Gilliland, Oxford (GB); Masahide Tone, Oxford (GB); Mark R Frewin, Oxford (GB); Louise Walsh, Cambridge (GB)

(73) Assignee: Isis Innovation Limited, Oxford (GB)

( * ) Notice: Subject to any disclaimer, the term of this patent is extended or adjusted under 35 U.S.C. 154(b) by 764 days.

(21) Appl. No.: 11/180,631

(22) Filed: Jul. 14, 2005

(65) Prior Publication Data

US 2006/0018898 A1    Jan. 26, 2006

Related U.S. Application Data (62) Division of application No. 09/125,460, filed as application No. PCT/GB97/00472 on Feb. 20, 1997, now abandoned.

(30) Foreign Application Priority Data

Feb. 20, 1996   (GB) .................................. 9603507.6

(51) Int. Cl.
    *A61K 39/00*      (2006.01)
(52) U.S. Cl.
    USPC ....................................................... 424/133.1
(58) Field of Classification Search .. 435/7.2; 424/130.1
    See application file for complete search history.

(56) References Cited

U.S. PATENT DOCUMENTS

| 5,846,534 | A | 12/1998 | Waldmann et al. |
| 5,858,725 | A | 1/1999 | Crowe et al. |
| 6,054,297 | A | 4/2000 | Carter et al. |

FOREIGN PATENT DOCUMENTS

| EP | 0328404 | 8/1989 |
| WO | 9307899 | 4/1993 |
| WO | 9310817 | 6/1993 |

OTHER PUBLICATIONS

William E. Paul, M.D. Fundamental Immunology 242. 3d ed. 1993.*
Pozzilli et al. (Met Res Rev, 16:306-307, 2000).*
Clark (Imm Today, 21(8):397-402, 2000).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Rudikoff et al., *PNAS*, 7, 9, pp. 1979-1983 (1982).
Isaacs and Waldman, "Helplessness as a strategy for avoiding antiglobulin responses to therapeutic monoclonal antibodies", *Therapeutic Immunology*, vol. 1, pp. 303-312 (XP000674792)(1994).
Gram H et al, "In Vitro Selection and Affinity Maturation of Antibodies from a Naive Combinatorial Immunoglobulin Library", *Proceedings of The National Academy of Sciences of Usa*, vol. 89, No. 8, pp. 3576-3580 (XP000384398) (Apr. 1992).
Riechmann et al., "Reshaping human antibodies for therapy", *Nature*, vol. 332, pp. 323-327, (XP002032968)(Mar. 1988).
Benjamin et al., "Tolerance to rat monclonal antibodies:", *J.Exp. Med.*, vol. 163, pp. 1539-1552 (XP000674798)(Jan. 1986).
Hoogenboom et al., "Multi-subunit proteins on the surface of filamentous phage: methodolgies for displaying antibod (Gab) heavy and light chains", *Nucleic Acids Research*, vol. 19, No. 15, pp. 4133-4137,(XP002032967)(Jun. 1991).
Lockwood et al., "Monoclonal antibody therapy in systemic vasculitis" *Clinical Research*, vol. 38, No. 2, p. o-2 (XP002032969)(1990).
Higuchi, "Using PCR to engineer DNA", *EERLICH:PCR Technology*, Chapter 6, pp. 61-70, Stockton Press, US, New York (XP002033036 166780)(1990).
Aucihncloss, Bach and Auchincloss (EDS.), *Transplantation Immunology*, Wiley Giss, New York, Chapter 11, p. 211-218 (1995).
B.A. Fields, et al., "Molecular Basis of Antigen Mimicry by an Anti-idiotope", *Nature*, 374(6524), pp. 739-742 (abstract)(Apr. 20, 1995).
Thomas B. Lavoie, et al., "Experimental Analysis by Site-directed Mutagenesis of Somatic Mutation Effects on Affon and Fine Specificity in Antibodies Specific for Lysozyme", *J. of Immunology*, vol. 148, No. 2, pp. 503-513 (Jan. 1, 1992).
Robert E. Hawkins, et al., "The Contribution and Contact and Non-contact Residues of Antibody in the Affinity of Binding to Antigen", *J. Mol. Biol.*, vol. 234, pp. 958-964 (1993).

* cited by examiner

*Primary Examiner* — Brad Duffy
(74) *Attorney, Agent, or Firm* — Wenderoth, Lind & Ponack, L.L.P.

(57) ABSTRACT

This invention relates to an antibody which is modified version of a therapeutic antibody with affinity for a cell-surface antigen, the antibody having reduced affinity for the antigen compared with the therapeutic antibody as a result of a modification or modifications to the antibody molecule, wherein the antibody is capable of inducing immunological tolerance to the therapeutic antibody. The invention further relates to a method of inducing immunological tolerance to a therapeutic antibody, comprising administering to a patient an antibody which is a modified version of the therapeutic antibody and which has reduced affinity for the antigen as compared with the therapeutic antibody.

13 Claims, 4 Drawing Sheets

PCR mutagenesis strategy

Figure 3

A. "Wild-type" Campath-1H heavy chain in pGEM9zf remove PstI-BstXI fragment

B. Substitute fragments carrying mutations mutant fragments

Figure 4

Schematic representation of a monovalent sFv-Ig minimal mutant

Note: Although this figure shows expression of the sFv in the VL-VH orientation, it is also possible to switch the orientation to VH-VL. In some cases this has been shown to increase expression levels.

SEQUENCE LISTING

<160> NUMBER OF SEQ ID NOS: 7

<210> SEQ ID NO 1
<211> LENGTH: 19
<212> TYPE: PRT
<213> ORGANISM: Artificial Sequence
<220> FEATURE:
<223> OTHER INFORMATION: SYNTHETIC SEQUENCE

<400> SEQUENCE: 1

Phe Ile Arg Asp Lys Ala Lys Gly Tyr Thr Thr Glu Tyr Asn Pro Ser
1               5                   10                  15

Val Leu Gly

<210> SEQ ID NO 2
<211> LENGTH: 19
<212> TYPE: PRT
<213> ORGANISM: Artificial Sequence
<220> FEATURE:
<223> OTHER INFORMATION: SYNTHETIC SEQUENCE

<400> SEQUENCE: 2

Phe Ile Arg Asp Asp Ala Lys Gly Tyr Thr Thr Glu Tyr Asn Pro Ser
1               5                   10                  15 val leu Gly

<210> SEQ ID NO 3
<211> LENGTH: 19
<212> TYPE: PRT
<213> ORGANISM: Artificial Sequence
<220> FEATURE:
<223> OTHER INFORMATION: SYNTHETIC SEQUENCE

<400> SEQUENCE: 3

Phe Ile Arg Lys Lys Ala Lys Gly Tyr Thr Thr Glu Tyr Asn Pro Ser
1               5                   10                  15

Val Leu Gly

<210> SEQ ID NO 4
<211> LENGTH: 19
<212> TYPE: PRT
<213> ORGANISM: Artificial Sequence
<220> FEATURE:
<223> OTHER INFORMATION: SYNTHETIC SEQUENCE

<400> SEQUENCE: 4

Phe Ile Arg Asp Lys Ala Asp Gly Tyr Thr Thr Glu Tyr Asn Pro Ser
1               5                   10                  15

Val Leu Gly

<210> SEQ ID NO 5
<211> LENGTH: 19
<212> TYPE: PRT
<213> ORGANISM: Artificial Sequence
<220> FEATURE:
<223> OTHER INFORMATION: SYNTHETIC SEQUENCE

<400> SEQUENCE: 5

Phe Ile Arg Asp Asp Ala Asp Gly Tyr Thr Thr Glu Tyr Asn Pro Ser
1               5                   10                  15

Val Leu Gly

<210> SEQ ID NO 6
<211> LENGTH: 19
<212> TYPE: PRT
<213> ORGANISM: Artificial Sequence
<220> FEATURE:
<223> OTHER INFORMATION: SYNTHETIC SEQUENCE

<400> SEQUENCE: 6

Phe Ile Arg Lys Asp Ala Asp Gly Tyr Thr Thr Glu Tyr Asn Pro Ser
1               5                   10                  15

Val Leu Gly

<210> SEQ ID NO 7
<211> LENGTH: 19
<212> TYPE: PRT
<213> ORGANISM: Artificial Sequence
<220> FEATURE:

-continued

```
<223> OTHER INFORMATION: SYNTHETIC SEQUENCE

<400> SEQUENCE: 7

Phe Ile Ala Lys Asp Ala Lys Gly Tyr Thr Thr Glu Tyr Asn Pro Ser
1               5                   10                  15

Val Leu Gly
```

ANTIBODY VARIANTS

This application is a divisional of Ser. No. 09/125,460, filed Aug. 19, 1998, now abandoned, which is a 371 U.S. National Stage of International Application No. PCT/GB 97/00472, filed Feb. 20, 1997.

This invention relates to modified antibodies for inducing immunological tolerance in human beings or animals.

Antibodies, or immunoglobulins, comprise two heavy chains linked together by disulphide bonds and two light chains, each light chain being linked to a respective heavy chain by disulphide bonds. Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain. The constant domains in the light and heavy chains are not involved directly in binding the antibody to antigen.

The variable domains of each pair of light and heavy chains form the antigen binding site. The variable domains of the light and heavy chains have the same general structure; each domain comprises four framework regions, whose sequences are relatively conserved, connected by three complementarity determining regions (CDRs). The CDRs are held in close proximity by the framework regions. CDRs from adjacent light and heavy chain variable domains together contribute to the formation of the antigen binding site.

BACKGROUND OF THE INVENTION

Antibodies directed to specifically chosen antigens have been used in the treatment of various conditions. For example, Campath-1 monoclonal antibodies (mAb) have been used successfully to induce remissions in lymphoma and leukemia patients and for the treatment of rheumatoid arthritis and vasculitis. The target antigen, CD52 (also referred to as CDw52; see e.g. Xia et al., 1991), is a GPI-anchored glycoprotein of lymphocytes and monocytes (and parts of the male reproductive system). It has an exceptionally short peptide sequence of 12 amino acids and a single, complex, N-linked oligosaccharide at Asn3 (Hale et al, 1990; Xia et al, 1991). CD52 is a good target for antibody-mediated killing and is therefore an effective cell surface molecule for various therapeutic regimens in which reduction in lymphocytes is an objective (e.g. removal of cells from donor bone marrow to prevent graft-versus-host disease, treatment of leukemia and lymphoma, and immuno-suppression).

Several rat anti-human CD52 Campath-1 mAb were generated by fusion of the Y3 rat myeloma line with spleen cells from a rat immunized with human T lymphocytes (Hale et al, 1983). Although the clinical effectiveness of rat Campath-1 mAb has been demonstrated regularly, many patients mounted an anti-antibody (antiglobulin) response against the xenogeneic protein that prevented retreatment with the therapeutic antibody. Antibody therapy is often limited by the antiglobulin response. The anti-idiotypic component (anti-Id; directed against the Ab V regions and in particular the Ab-combining site) inhibits the binding of the Ab to its target while both the anti-Id and the anti-isotypic component (directed against the constant regions) act to accelerate antibody clearance. A major concern is the neutralizing effect of the antiglobulin response. As with antiglobulin responses in general, anti-Id responses interfere with the clinical potency of a therapeutic Ab by forming Ab aggregates that are rapidly cleared from the circulation, reducing the chance for interaction with target antigen. Unfortunately, most antiglobulin sera contain anti-Id antibodies. This has been demonstrated for a number of therapeutic mAb and is especially noted after repeated treatments.

To reduce the immunogenicity of the rat IgG2b Campath-1 antibody, YTH34-5, the gene fragments encoding the VL and VH were humanized by "CDR grafting" of the rodent hypervariable regions onto human framework regions (Jones et al, 1986; Reichmann et al, 1988). This was carried out by splicing the CDR sequences encoding the rat Campath-1 antibody onto sequence encoding human framework backbone provided by the crystallographically solved myeloma proteins NEW (for the VH) and REI (for the VL). The resulting protein had low antigen-binding titre and modelling of the humanized V-region showed that residue 27 in the VH framework sequence was critical for preserving the loop structure of CDR1. This residue was changed from the residue found in NEW (Ser) back to the rat residue Phe which resulted in restoration of antigen binding. During the to modelling, an additional change (NEW residue Ser to the rat residue Thr) was also suggested. However, in functional assays this substitution had no effect on antigen binding, but the double mutant (Ser27 to Phe27 and Ser30 to Thr30) expressed the most protein and therefore was used to produce therapeutic humanized Campath-1 Ab, designated Campath-1H (Reichmann et al, 1988). As many human VH frameworks have threonine at position 30, this change was not considered an additional risk to the antibody's immunogenicity. The humanized VL and VH were then genetically fused with human light chain and heavy chain constant regions, respectively. In summary, the humanized Campath-1 antibody consists of human residues at all positions except those encoding the 3 CDRs of the light chain, the 3 CDRs of the heavy chain, and residues Phe27 and Thr30 in VH of the heavy chain.

In clinical trials, the humanized version (Campath-1H) was found to be much less immunogenic than the rat IgG2b Campath-1 antibody. Humanization reduces the immunogenicity of rodent mAb, although both the idiotype and the allotype of a humanized mAb might stilt be targets for humoral responses. Sensitization to idiotype has indeed been documented in some allotype-matched recipients of Campath-1 H (Isaacs et al, 1992; Lockwood et al, 1993). These responses were revealed by the presence of anti-id in the patients' sera. One patient generated high-titre anti-Id that crossreacted on the entire panel of CD52 mAb. Humanized Campath-1 antibodies are described in EP 0 328 404 the teachings of which are incorporated herein by reference, in their entirety.

One strategy to further reduce the immunogenicity of Campath-1H might be to re-graft the 6 CDR loops onto well-characterized human germline framework regions. The majority of the humanized V regions so far have used rearranged V-genes as acceptor framework sequence. This was the case for Campath-1H as framework sequences from myeloma proteins were used to provide acceptor sequences for both VH and VL. Rearranged V-genes often contain somatic mutations, acquired during the process of affinity maturation. These will be unique to the individual from which the rearranged genes were derived and therefore may be seen as foreign in another individual. However, there is a possibility that regrafting may introduce new idiotypic epitopes, formed by the junctional regions encompassing CDR residues and new framework residues. Furthermore, humanization alone may not solve the problem of anti-Id responses because the human population is outbred and it is unlikely that all patients will be tolerant to a given humanized mAb. Even in antibody constant regions, there are a number of different alleles which carry allotypic markers to which naturally occurring antiglobulin responses can be demonstrated. The problem is more complex for V-region segments, which show a higher degree of variation both in allotype and haplotype in comparison to constant regions.

Another approach is to induce tolerance to the potentially foreign peptides contained within the Campath-1H V-region. We know that the antiglobulin response is itself a B-cell response which is CD4+ T-cell dependent. Isaacs and Waldmann (1994) demonstrated that mice deprived of CD4+ Tells were unable to respond to a foreign cell-binding mAb (rat anti-mouse CD8 mAb). CD4+ Tell depletion was carried out by adult thymectomy combined with administration of a depleting CD4 mAb. In these mice, the response to subsequently administered mAb or SRBC was measured. CD4+ T-cell deficient mice failed to make either an antiglobulin response or an anti-SRBC response, demonstrating that the anti-Ig response, like the anti-SRBC response, is classically CD4+ T-cell dependent. In order to generate T-cell help and to get the appropriate T-cell response, the adminstered Ab must be processed as a protein antigen and presented, presumably in the context of an MHC class II molecule, by a suitable antigen presenting cell. Therefore, two main strategies can be adopted to decrease the immunogenicity of a humanized V-region. (1) We can "silence" the antibody molecule itself, adopting strategies to eliminate any potential T helper epitopes, or (2) we can present all the potential T helper epitopes in a manner that induces tolerance instead of reactivity to those epitopes.

"Silencing" the Antibody Molecule:

a) In theory, we might be able to silence the antibody itself so that the immune system will not recognize foreign determinants. This would be possible if we could scan the VL and VH amino acid sequences for motifs that could bind to MHC class II molecules. If we could thus identify key residue(s) in a potential class II peptide that were not involved in antibody specificity or affinity, then it/they could be changed by site-directed mutagenesis to residue(s) that did not allow association with class II molecules. T helper peptides are not random, and any protein has only a limited number of peptides capable of binding to MHC class II molecules, and also to T-cell antigen receptors. However, this is not possible at present because class II-binding peptides are not yet characterized to a sufficient degree to be identified by scanning protein sequences. This is in part due to the heterogeneous nature of class II peptides. Naturally processed peptides isolated from MHC class II molecules are generally larger in size, variable in length and have both ragged ends at C- and N-termini in comparison to processed peptides isolated from MHC class I molecules. Whereas class derived peptides are mostly of uniform length of 8-9 amino acid residues, MHC class II-associated peptides range from 12-24 amino acids (Rudensky et al, 1991; Hunt et al, 1992; Rudensky and Janeway, 1993). Class I-derived peptides have sequence motifs with specific anchor residues in certain positions allowing their side chains to fit in the binding pockets of the peptide-binding groove, and the peptide-binding groove is closed at both ends. In contrast, class II peptides are bound in an extended conformation that projects from both ends of an "open-ended" antigen-binding groove; a prominent non-polar pocket into to which an anchoring peptide side chain fits near one end of the binding groove (Brown et al, 1993).

b) Other strategies that might be adopted to "silence" the antibody if we could predict class II peptide-binding motifs. For example, one could include insertion of a protease cleavage site within any potential class II epitope to increase the chance of peptide degradation before they could be presented in the context of class II. Alternatively, insertion of motifs into a V-region such as Gly-Ala repeats may inhibit the degradation of the V-region into peptides that could associate with class II molecules. In one system, it was shown that EBNA1 Gly-Ala repeats generated a cis-acting inhibitory signal that interfered with antigen processing during MHC class I-restricted presentation such that CTL recognition was inhibited (Levitskaya et al, 1995). Although either of these approaches may hold some promise in the future, they again rely on prediction of potential MHC class II peptides from protein sequence of humanized VL and VH regions and are therefore limited by insufficient knowledge regarding consensus motifs for class II peptides.

Inducing Tolerance to T Helper Epitopes

In lieu of sufficient knowledge regarding class II peptide motifs, we have turned our attention toward induction of tolerance to therapeutic antibodies. In 1986, Benjamin et al and Cobbold et al described an unexpected property of cell-binding mAb: whereas it was possible to induce tolerance to the Fc region (anti-isotype tolerance), the idiotype remained antigenic under equivalent conditions. Moreover, it was relatively easy to induce tolerance to non-cell binding mAb but cell-binding mAb were found to be very immunogenic.

Isaacs and Waldmann (1994) in a preliminary study used a non-cell-binding "mixed molecule" derivatives of a cell-binding Ab to induce tolerance to the wild-type form. The cell-binding antibody was an anti-CD8 mAb in a mouse model. The non-cell-binding derivatives were made by pairing the relevant L- and H-chains with an irrelevant H- or L-chain, respectively. The relevant H-chain paired with an irrelevant L-chain was obtained by limiting dilution cloning of the original hybridoma that was expressing a myeloma light chain (from the Y3 fusion partner), as well as the specific anti-CD8 H- and L-chains. A variant of the hybridoma that expressed the myeloma L-chain and the specific anti-CD8 H-chain but no anti-CD8 L-chain was obtained. A clone expressing the relevant L-chain only was also obtained in this manner. That clone was then fused to a hybridoma expressing an irrelevant specificity (anti-human CD3) and a variant was selected that expressed the relevant anti-CD8 L-chain with the irrelevant anti-CD3 H-chain. Because proteins are processed into peptides prior to presentation to T-cells, helper peptides from antigen-specific H- and L-chains would be "seen" by T-cells, regardless of their partner chain. However, in this case, there was no advantage in tolerance induction using non-cell-binding mixed molecule derivatives of a therapeutic mAb in vivo compared to an isotype-matched control, suggesting that in the strain of mice used, most (or all) of the helper epitopes were located within the constant region.

In practice, using these "mixed molecules" of antigen-specific and irrelevant immunoglobulin chains for human therapy would not be feasible because the irrelevant H- and L-chains would carry some helper epitopes themselves, thus complicating the ability to achieve tolerance to the relevant H- and L-chains. Nor would one expect to tolerize those B-cells which "see". idiotypic determinants formed by the combination of the relevant H- and L-chains of the antibody.

Campath-1 is a cell-binding mAb, and an effective tolerogen for use with it, such as a non-cell-binding form of the therapeutic mAb would therefore be advantageous. The same goes for other therapeutic antibodies which have cell-binding properties, and non-cell-binding variants thereof.

The Invention

The invention therefore provides an antibody which is a modified version of a therapeutic antibody with affinity for a cell-surface antigen, said antibody having reduced affinity for the antigen compared with the therapeutic antibody as a result of a modification or modifications to the antibody molecule, wherein the antibody is capable of inducing immunological tolerance to the therapeutic antibody.

Preferably, the affinity of the antibody according to the invention for the antigen is reduced to 50% or less of the affinity of the therapeutic antibody for the antigen. More preferably, the affinity is reduced to 10% or less, or to 1% or less of the affinity of the therapeutic antibody. The affinity needs to be sufficiently reduced to allow the antibody according to the invention to act as a tolerogen with respect to the therapeutic antibody. The term "non-cell-binding variant" is used herein to refer to antibodies according to the invention, although antibodies according to the invention may still have some binding affinity for the cell surface antigen.

The ability of the antibody according to the invention to induce immunological tolerance to a therapeutic cell-binding antibody relies on the presence in the non-cell-binding antibody of at least one epitope also present in the therapeutic antibody, which induces an immune response in the intended patient.

The non-cell-binding antibody is preferably capable of tolerising to anti-idiotypic responses, at least to the V domain hypervariable regions of the therapeutic antibody and preferably also to the framework regions. Thus it is desirable that the tolerising antibody has an amino acid sequence similar to the therapeutic antibody in those regions. Preferably there is >90%, or >95% or >99% amino acid sequence identity between the variable domains of the non-cell-binding antibody and the therapeutic antibody. Most preferably the differences are restricted to any amino acid to substitution(s) required to sufficiently reduce antigen binding affinity in the non-cell-binding antibody.

Preferably also the non-cell-binding antibody is capable of inducing tolerance to the constant regions of the therapeutic antibody. Thus, it is preferred that the constant domains of the non-cell-binding antibody are similar to those of the therapeutic antibody, having for example >90% or >95% or >99% amino acid sequence identity. Most preferably, the constant domains of the non-cell-binding antibody and the therapeutic antibody are identical and are thus matched allotypically.

The invention further provides fragments of an antibody described herein, the fragments having tolerance-inducing capability. Such fragments include monovalent and divalent fragments such as Fab, Fab' and $F(ab')_2$ fragments. Also included are single chain antibodies. The preferred features of such fragments are as described herein in relation to non-cell-binding antibodies according to the invention. The non-cell-binding fragments may be for use with corresponding therapeutic antibody fragments, or with therapeutic antibody molecules.

The reduced binding affinity of the non-cell-binding antibodies may be achieved in a variety of ways. In the preferred embodiment described herein, an alteration in the CDRs comprising one or two or more amino acid substitutions reduces binding affinity, Alternatively, amino acid substitutions in other parts of the antibody molecule may be used to reduce binding affinity. For example, amino acid substitutions in the framework regions are known to significantly affect binding affinity (Reichmann et al 1988). Another alternative is a monovalent form of the therapeutic antibody. Monovalent antibodies have reduced binding affinity compared to their bivalent counterparts. Monovalent forms may be for example Fab fragments, or single chain antibodies, or any other genetically engineered antibody fragments retaining a single binding site. Monovalent variants can also be produced by mutating the cysteine residue which participates in interchain (H-H) disulphide formation (e.g., cys→ser or cys→ala). The reduction in binding affinity of a monovalent antibody compared to its bivalent counterpart may be sufficient to enable tolerance induction. Preferably, the monovalent antibody is either incapable of binding Fc receptors, or incapable of binding complement component C1q, or both. Either or both of these properties can be introduced by suitable mutations (see e.g., Morgan et al., WO 94/29351, published 22 Dec. 1994 and Winter et al., EP 0 307 434 B1).

The non-cell-binding antibodies or fragments according to the invention may thus be one of a variety of types of antibodies or fragments, including genetically engineered antibodies or antibody fragments. In addition, the antibodies or fragments will generally be from a mixture of origins. For example, they may be chimeric e.g. human constant regions with rat variable domains; or humanised or CDR grafted or otherwise reshaped (see, e.g., Cabilly et al., U.S. Pat. No. 4,816,567; Cabilly et al., European Patent No. 0 125 023 B1; Boss et al., U.S. Pat. No. 4,816,397; Boss et al., European Patent No. 0 120 694 B1; Neuberger, M. S. et al., WO 86/01533; Neuberger, M. S. et al., European Patent No. 0 194 276 1; Winter, U.S. Pat. No. 5 225 539; Winter, European Patent No. 0 239 400 B1; Queen et al., U.S. Pat. No. 5,585, 089; Queen et al., European Patent No. 0 451 216 B1; Adair et al., WO 91/09967, published 11 Jul. 1991; Adair et al., European Patent No. 0 460 167 B1; and Padlan, E. A. et al., European Patent No. 0 519 596 A1. See also, Newman, R. et al., *Biotechnology,* 10: 1455-1460 (1992), regarding primatized antibody, and Huston et al., U.S. Pat. No. 5,091,513; Huston et al, U.S. Pat. No. 5,132,405; Ladner et al., U.S. Pat. No. 4,946,778 and Bird, R. E. et al., *Science,* 242: 423-426 (1988) regarding single chain antibodies). Campath-1H is considered humanised although it contains two amino acid substitutions in the framework regions.

Ideally, the antibody according to the invention is as close as possible to the therapeutic antibody on which it is based. Administration of such a "minimal mutant" prior to injection of the cell-binding therapeutic mAb can be used to tolerise to all T- and most B-cell epitopes in the therapeutic mAb. Classic experiments indicate that tolerance is maintained more effectively by T-cells than by B-cells. But since most B-cell responses including the anti-id response require T-cell help, even if a B-cell is responsive to a given antigen, antibody production will be determined by the state of responsiveness of the T-cells (Chiller et al, 1971). Thus, it will be preferable to use a non-cell-binding variant which contains the minimum differences needed to reduce its affinity for the cell-surface antigen sufficiently to enable it to be used as a tolerogen. By using techniques such as X-ray crystallography, computer modeling and site-directed mutagenesis, and also genetic methods such as phage display, it will be possible to design suitable non-cell-binding variants for any cell-binding therapeutic antibody.

The antibody according to the invention is preferably in biologically pure form, desirably being at least 95% (by weight) free of other biological materials.

As used herein, the term "cell-surface antigen" means an antigen which is found on, cell surfaces, but not necessarily exclusively on cell surfaces.

The term "therapeutic antibody" is used herein to refer to an antibody which may be administered to humans or animals to have a desired effect in particular in the treatment of disease. Such therapeutic antibodies will generally be monoclonal antibodies and will generally have been genetically engineered.

In another aspect the invention comprises a composition for administration to a patient comprising an antibody as described herein, together with a physiologically acceptable diluent or carrier.

In a further aspect, the invention provides a host cell or cell line which expresses an antibody as herein described and use of such a host cell or cell line for the production of such an antibody.

Additional aspects of the invention include the use of an antibody as described herein in the manufacture of medicament for the induction of tolerance, in particular tolerance to a therapeutic antibody.

In attached figures:

FIG. 1 shows the Campath-1H heavy chain minimal mutant constructs prepared as described in the Examples. The sequence of 19 amino acids shown in FIG. 1 is set forth in the attached Sequence Listing as SEQ ID NO: 1. Mutant 1 is the amino acid sequence of SEQ ID NO: 1 wherein, at position 5, Lys is substituted for Asp. Mutant 2 is the amino acid sequence of SEQ ID NO: 1 wherein, at position 4, Asp is substituted for Lys. Mutant 3 is the amino acid sequence of SEQ ID NO: 1 wherein, at position 7, Lys is substituted for Asp. Mutant 4 is the amino acid sequence SEQ ID NO: 1 wherein, at positions 5 and 7, Lys is substituted for Asp. Mutant 5 is the amino acid sequence of SEQ ID NO: 1 wherein, at position 4, Asp is substituted for Lys, and, at positions 5 and 7, Lys is substituted for Asp. Mutant 6 is the amino acid sequence SEQ ID NO: 1 wherein, at position 3, Arg is substituted for Ala, at position 4, Asp is substituted for Lys, and, at position 5, Lys is substituted for Asp.

Using Rational Design to Create a "Minimal Mutant"

In one embodiment for producing a non-cell-binding variant of a therapeutic mAb, amino acid residues which are involved in binding to target antigen are identified. Relative to the number of residues that comprise the VL and VH domains, those that are directly involved in interactions with antigen are small in number (Novotny et al, 1983). And although the Ab-combining site is made up of 6 hypervariable loops, 1 or 2 of those loops may dominate in that interaction. If a key residue or residues can be identified, it/they can be changed by site-directed mutagenesis to a residue that will reduce (reduce or abolish) antigen-binding. Because these residues will most likely be found within the hypervariable loop structures and not in the framework sequence supporting those loops, small changes may not significantly disrupt the overall structure of the Ab.

Model Building of Ag-binding Sites to Define Key Residues for Mutagenesis:

Because the constant regions and variable regions of Ab molecules are very similar in sequences and structures, general principles regarding Ab structure have been defined using relatively few solved crystal structures. To date, approximately 50 structures of Ab fragments have been included in the Brookhaven Protein Data Bank, and of these, 20% have been refined to a resolution of 2.0 angstroms or better. As the structural knowledge base increases, comparative Ab modelling (modelling by homology) becomes more reliable since there is a greater choice of structural templates. Variable regions (VL and VH) of different Ab structures can be combined as a structural template after superimposing their most conserved residues. Side chain conformations of buried residues are then modelled. The CDR loops are modelled by identification of structurally similar loop templates (often loops with the same length and similar sequence have similar backbone conformations). These CDR sequences often fall into canonical loop motifs (excluding H3, between 50 and 95% of murine VL (kappa) and VH have loop sequences consistent with classified canonical motifs). Canonical loop backbones can then be spliced onto the model of the framework and CDR side-chain conformations can be modelled based on conformations of residues found at corresponding positions in other loops of the same canonical structure. Finally the model is often refined using computer programs that minimize troublesome stereochemical constraints.

Comparative model building is becoming widely used as the size of the structural database increases, providing a greater range of structural templates. Also, the greater range of computer programs available ensures that models are becoming increasingly accurate. For example, the solved crystal structure of Campath-1H was very close to the structure predicted by molecular modelling. We could predict from the to modelling data that mutations 1 and 2 described in the Examples were likely to have a detrimental effect on binding to CD52. The crystal structure confirmed these predictions and also predicted that mutation 3 could disrupt binding to CD52.

Obviously, to create a non-cell-binding version of a therapeutic Ab, it is desirable to start with a solved crystal structure, preferably co-crystallized with antigen so that the key contact residue(s) can be identified and substituted for residue(s) that destroy antigen binding. However, in many cases, a good molecular model could provide the necessary information. In cases where the molecular model is of poor quality (for example, if the appropriate structural templates do not exist in the databank), CDR swapping experiments (as described in the Examples) will provide information on which CDRs must be targeted for mutation. Alanine scanning mutagenesis (mutating each residue sequentially to Ala) through those regions could identify the key residue(s) involved in antigen-binding (Cunningham and Wells, 1989). If changing a single residue to Ala reduced but did not destroy binding, that position could be targetted for more drastic mutations (for example, a substitution that created in a charge difference) to further reduce binding, if desired.

Alternative methods for obtaining non-cell-binding versions of therapeutic antibodies include genetic techniques such as phage display using error prone PCR (Gram et al, 1992) and cycling of V-region genes (e.g. as sFv constructs) through a bacterial mutator strain (e.g. mutD5) (Low et al., 1996). Such genetic methods can provide powerful screening systems.

The invention will now be further described in the examples which follow. Although the specific example of Campath-1H is given in this document. the invention is not limited to antibodies based on Campath-1H. It is anticipated that other cell-binding therapeutic antibodies, especially those which would be given in repeated doses, will become more widely to accepted using this strategy.

EXAMPLES

A. Creating a "Minimal Mutant"

We have devised a method to determine which of the CDR loops of the humanized Campath-1 mAb are the most important ones for binding to CD52. Mutant VL or VH were genetically constructed in which each of the 6 hypervariable regions (as defined by Kabat et al (1987) using amino acid sequence alignments of V-regions in the protein databases) was individually swapped for the corresponding CDR from the V-region that had provided the human VL or VH acceptor sequence during humanization (REI and NEW, respectively).

The engineered V-regions were expressed as Fab fragments in *E coli* using the pHEN vector (Hoogenboom et al, 1991). In this system, the pelb leader sequence was used to direct protein expression to the periplasm, where association of L-chain and truncated H-chain occurs (Hoogenboom et al, 1991). When these Fab fragments were assayed for binding to immobilized CD52, it was found that swapping the (VH) CDR2 of NEW into the humanized Campath-1 Fab completely destroyed binding to CD52. Replacing (VH) CDR3 reduced binding to CD52 8-fold while replacing (VH) CDR1 and (VL) COR3 reduced binding 3-fold. No change in binding was detected when (VL) CDR1 or (VL) CDR2 were replaced. From these results, it appeared that (VH) CDR2 contained a key residue(s) necessary for antigen-binding. DNA encoding the "wild-type" humanized Campath-1H-chain (Reichmann et al. 1988) was used as PCR template for site-directed mutagenesis. This heavy chain sequence encodes human protein at all positions except the three VH CDR regions and positions 27 and 30 of the first framework region. We focussed on the H2 loop within VH CDR2 to make mutations which would abolish binding of the Ab to CD52. H2 is the actual loop structure (Chothia and Lesk, 1987) that is found within the 19 amino acid VH CDR2 denoted "hypervariable" by Kabat et al's definition (Kabat et al, 1987) (see FIG. 1). It is known that a few key residues in the loop and/or framework regions determine relatively few CDR loop conformations and canonical loop motifs have been identified for most CDR including VH CDR2 (Chothia and Lesk, 1987). Since it is the loop structures that stick out from the V-region β-barrel framework to make contact with antigen, mutations in the loop would have the greatest chance of destroying antigen binding whilst preserving Ab structure. In general, we restricted the changes to the H2 loop except for H-chain mut6 which contained an additional mutation in the residue immediately preceeding H2 as discussed in more detail below.

Figure 1:
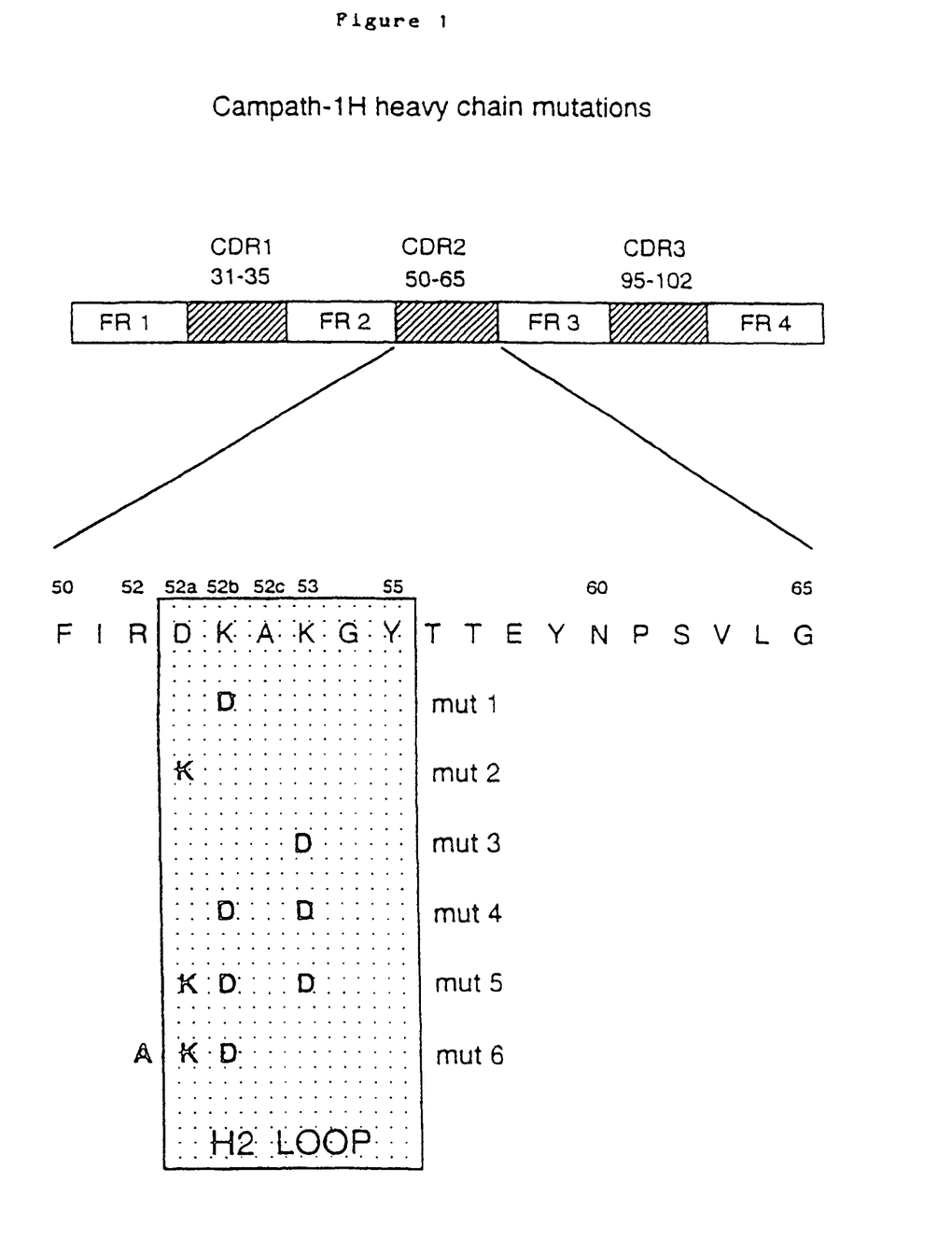

Summary of Campath-1H Heavy Chain Minimal Mutant Constructs (FIG. 1)

Mutation 1 (SEQ ID NO: 2) is a single charge difference at residue 52b from Lys to Asp relative to SEQ ID NO: 1. It was predicted from the molecular modeling of the Campath-1H Ab, and supported by the crystal structure, that the side chain of this residue is pointing out of the Ag binding pocket, towards the approach of antigen. Since the positive charge of the Lys is thought to interact with the negatively charged phosphate groups of the GPI anchor of CD52, it is possible that this single mutation will destroy antigen-binding.

Mutation 2 (SEQ ID NO: 3) is a single charge difference at residue 52a from Asp to Lys. It was predicted from the molecular modeling of the Campath-1H Ab that this change could interfere with antigen-binding.

Mutation 3 (SEQ ID NO: 4) is a single charge difference at residue 53 from Lys to Asp. From the crystal structure of Campath-1H Ab, it is clear that the majority of this residue side chain is solvent accessible and therefore my be involved in the interaction with the negatively charged phosphate groups of the GPI anchor of CD52, as for mutation 1.

Mutation 4 (SEQ ID NO: 5) is a double mutation encompassing the individual substitutions of mutant 1 and 3 (Lys52b and Lys53 to Asp).

Mutation 5 (SEQ ID NO: 6) is a triple mutation encompassing the individual substitutions of mutant 1, 2 and 3 (three charge differences: Asp52a to Lys; Lys 52b and Lys53 to Asp).

Mutation 6 (SEO ID NO: 7) is a triple mutation encompassing the individual substitutions of mutant 1 and 2 (two charge differences: Asp52a to Lys; Lys52b to Asp), and an additional mutation of Arg52 to Ala. Residue 52 has been shown to differ between 3 different Campath-1 Ab of high, low and moderate affinity and may be therefore directly involved in affinity maturation. This in turn might suggest a role in antigen binding.

Figure 2:
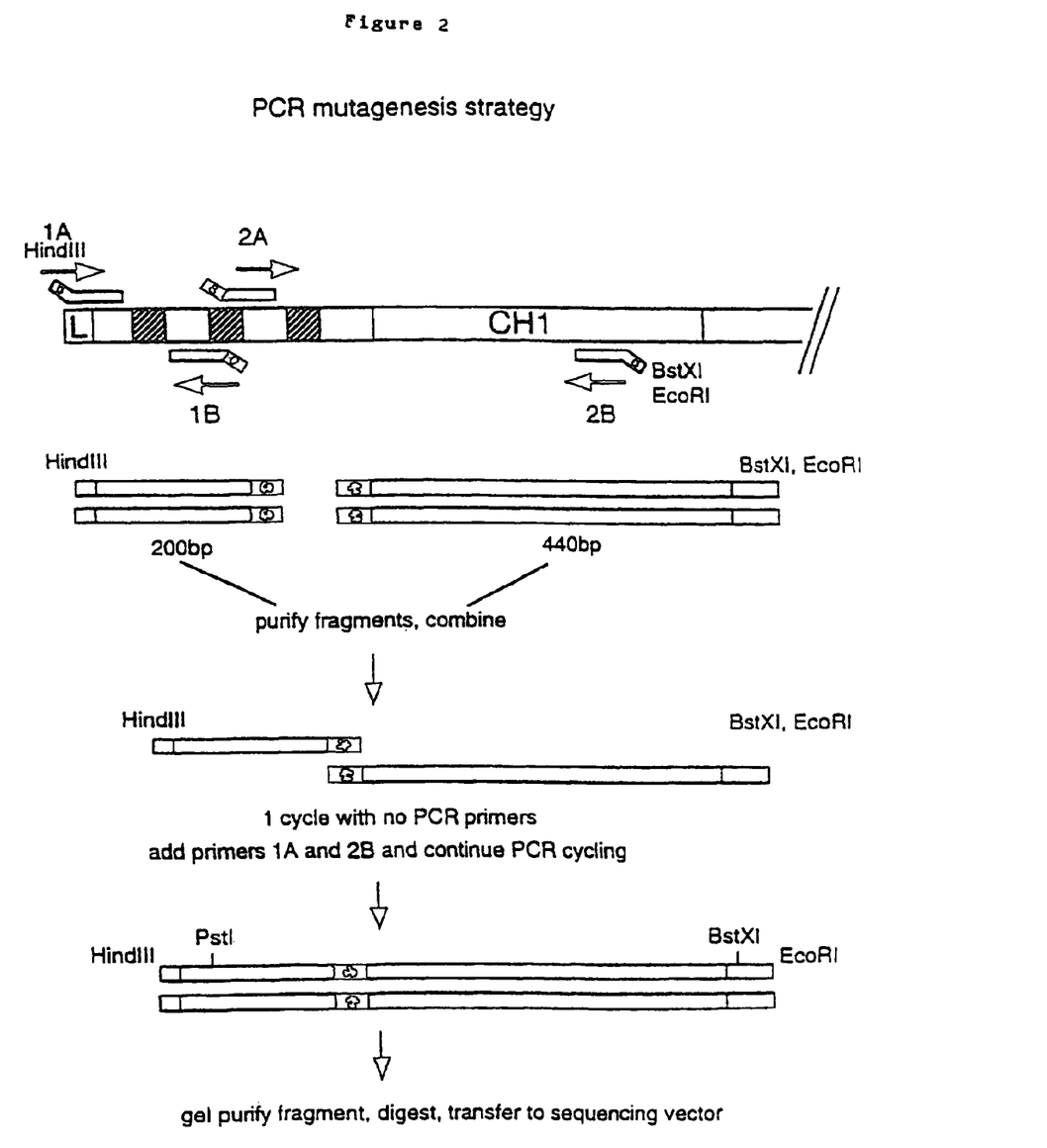
FIG. 2 shows the PCR mutagenesis strategy for preparing the mutant constructs of FIG. 1.
Figure 3:
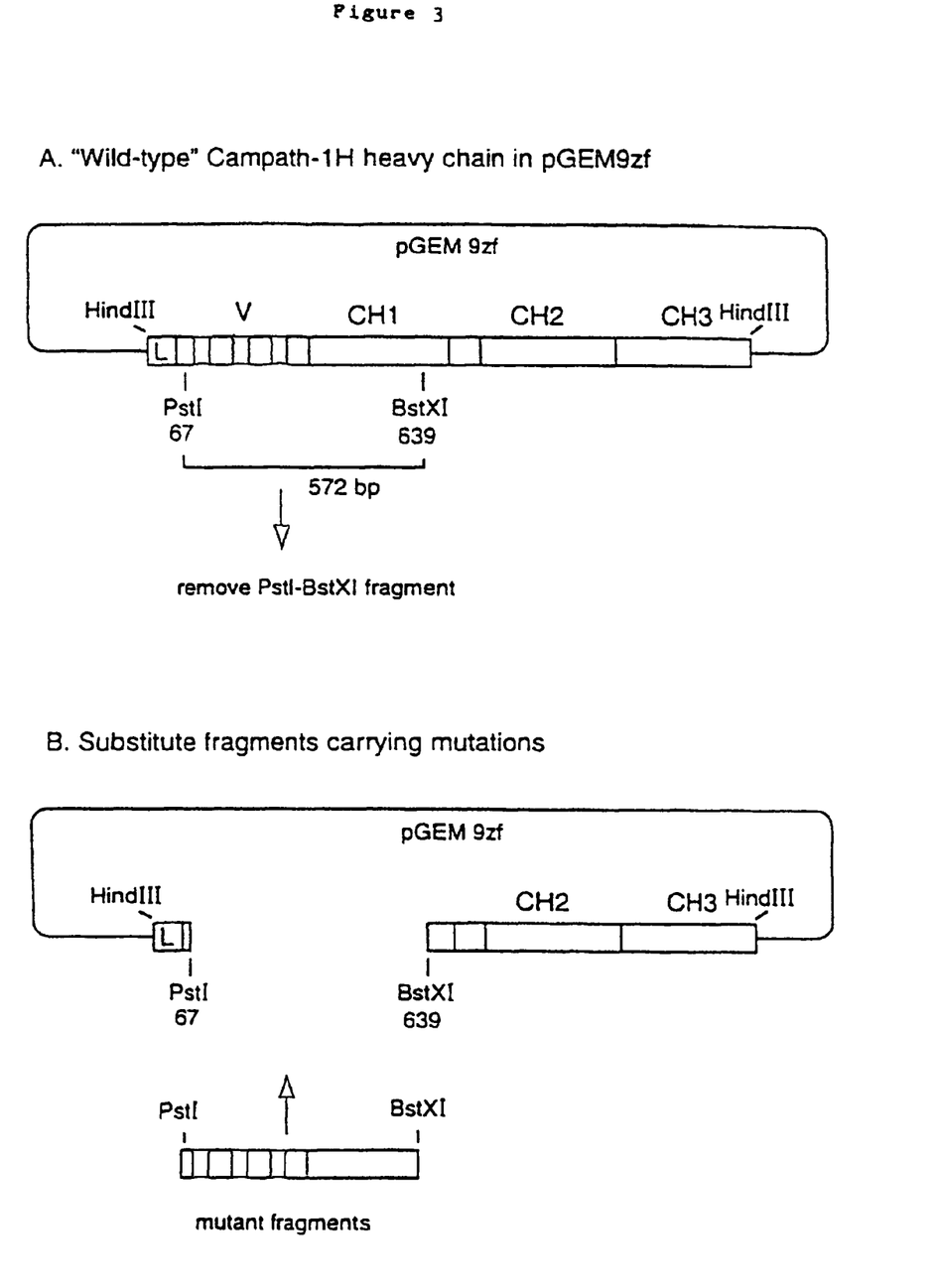
FIG. 3 shows pGEM9zf containing wild type Campath-1H heavy chain, and substitution of mutant fragments in the heavy chain.
Figure 4:
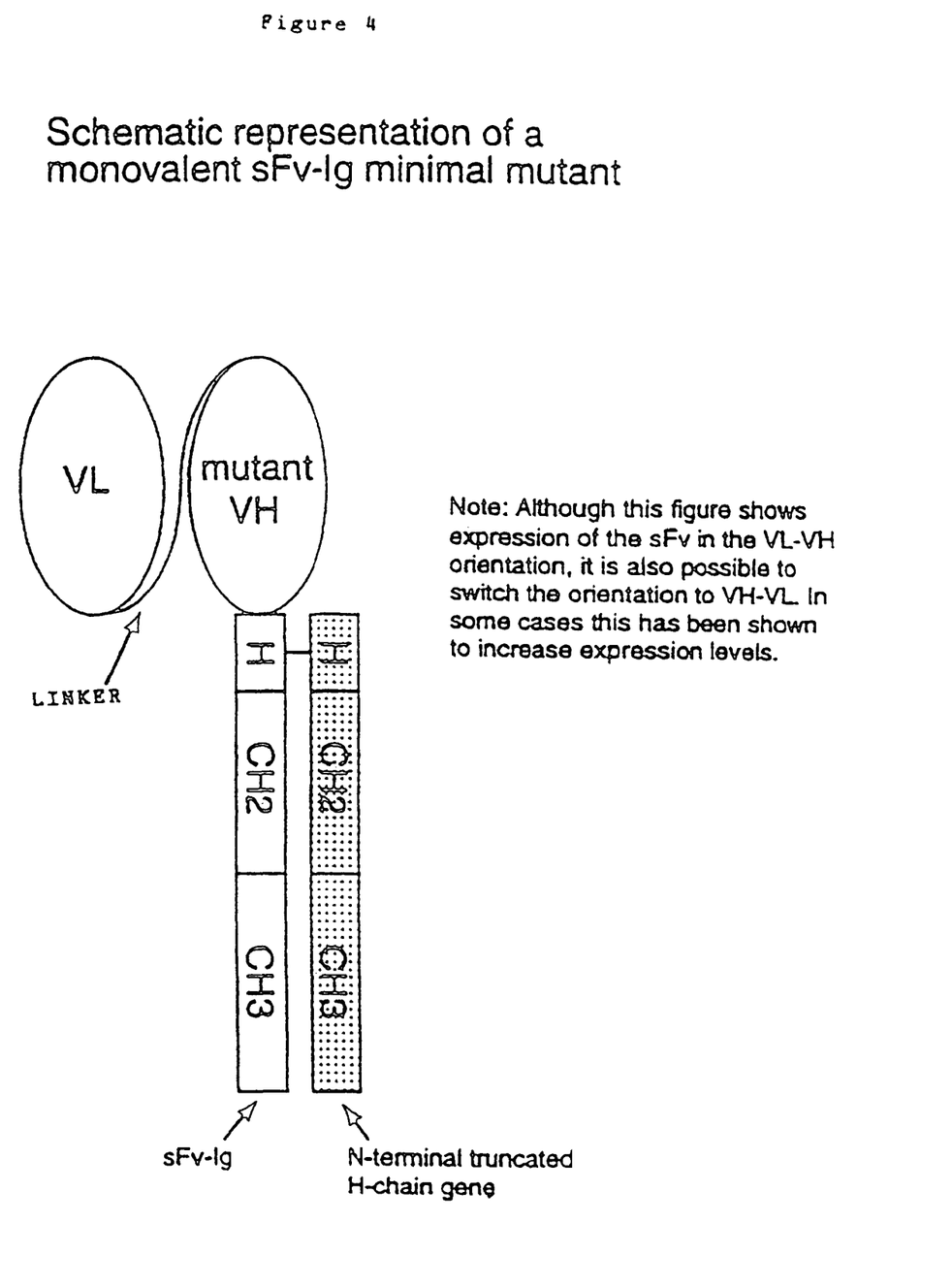
FIG. 4 shows a schematic representation of one embodiment of a monovalent non-cell-binding therapeutic antibody.

For each of these heavy chain mutations, the change(s) was/were encoded on oligonucleotide primers 1B and 2A (FIG. 2). PCR was carried out on "wild-type" Campath-1 heavy chain DNA using a 5' primer annealing to the leader sequence and containing an upstream HindIII site (primer 1A) and primer 1B to generate a 200 bp fragment. Similarly, primer 2B (annealing to CH1 and containing a BstXI site followed by an EcoRI site) and primer 2A, a 440 bp fragment was generated. These fragments were gel purified and then combined in a single PCR reaction. Primer 1A and primer 2B were added after the first cycle (thus allowing the 2 pieces of overlapping DNA to anneal before amplification). Following PCR, the fragments were gel purified and digested with HindIII and EcoRI and were transferred into intermediate sequencing vectors (PUC19 or pGEM3zf) for verification of sequence. A unique PstI site located in the Campath-1H VH and a unique BstXI site in the CH1 region allowed the mutant V-regions (and partial CH1 sequence) to be isolated as PstI-BstXI fragments such that the mutation(s) were encoded in six different DNA cassettes flanked by PstI and BstXI sites. To create the mutant Campath-1H heavy chains, the original heavy chain construct (in intermediate vector pGEM9zf) was cut with PstI and BstXI and the fragment was removed. The remaining DNA (encoding the Campath-1H heavy chain leader sequence and the V-region upsteam of the PstI site, plus the CH1 region downstream of the BstXI site followed by the hinge, CH2, CH3 in pGEM9zf) was gel purified (FIG. 3). Ligations were then set up in which each of the DNA cassettes containing the mutation(s) described above was joined to the gel purified pGEM9zf(PstI-BstXI cut Campath-1H heavy chain DNA. These six mutagenized Campath-1H heavy chains were then isolated by digestion with HindIII and gel purification, followed by ligation into HindIII cut mammalian expression vector pBAN-2. This vector is derived from the pNH316 vector that contains a neomycin selectable marker under the control of the mouse metallothionein promoter and the strong human β-actin promoter/polyadenylation signals for expression of the desired gene product (Page and Sydenham, 1991). As these fragments were introduced into a single HindIII restriction site, orientation of each fragment was checked by DNA sequencing.

Campath-1H Light Chain Construct for Co-transfection:

DNA encoding the humanized "wild type" Campath-1H light chain (human sequence at all residues except the three CDR in the V-region) was isolated from an intermediate vector as a HindIII to EcoRI fragment. This fragment was gel purified and then ligated into HindIII-EcoRI cut mammalian expression vector pRDN-1. This vector is derived from the pLD9 vector that contains a "crippled" dihydrofolate reductase (dhfr) selectable marker (the enhancer element of the SV40 promoter has been removed to allow for increased levels of gene expression in the presence of methotrexate) and the strong human β-actin promoter/polyadenylation signals for expression of the desired gene product (Page and Sydenham, 1991).

Co-transfection of Campath-1H Light Chain DNA and Mutant Heavy Chain DNA:

The expression system used to produce high levels of humanized Campath-1H Ab in the past is the widely used mammalian expression system featuring gene amplification by the use of dihydrofolate reductase (dhfr) deficient Chinese hamster ovary (CHO) cells and the use of strong β-actin promoters for selection and amplification of the desired gene products (Page and Sydenham, 1991).

The following transfections (TF) were carried out;
TF1: mock ("empty" pRDN-1 plus "empty" pBAN-2)
TF2: Light chain only (Light-chain/pRDN-1 plus "empty" pBAN-2)
TF3: Light chain/pRDN-1 plus H chain mutant 1/pBAN-2
TF4: Light chain/pRDN-1 plus H chain mutant 2/pBAN-2
TF5: Light chain/pRDN-1 plus H chain mutant 3/pBAN-2
TF6: Light chain/pRDN-1 plus H chain mutant 4/pBAN-2
TF7: Light chain/pRDN-1 plus H chain mutant 5/pBAN-2
TF8: Light chain/pRDN-1 plus H chain mutant 6/pBAN-2
TF9: Light chain/pRDN-1 plus H chain "wild-type"/pBAN-2

DNA (20 µg of light chain/pRDN-1 plus 20 μg of heavy chain/pBAN-2) was mixed in a sterile eppendorf, ethanol precipitated, and rinsed twice with 70% ethanol. DNA pellets were resuspended in sterile Tris-EDTA.

For each transfection, the DNA was diluted with 60 μl of 20 mM HEPES (pH 7.4) in a 5 ml polystyrene tube. In another tube, 120 μl of DOTAP liposomal transfection reagent (Boehringer Mannheim) was diluted with 80 μl of 20 mM HEPES (pH 7.4). Then the DNA/HEPES was added to the diluted DOTAP, mixed gently, and left at room temperature for 15 min. Culture medium (IMDM+5% FCS+HT) was aspirated from a T75 flask containing dhfr deficient CHO cells growing at approximately 50% confluency. The DNA/DOTAP was then added to the flask along with 10 ml fresh culture medium. The flask was cultured for 24 h at 37° C. in 5% $CO_2$. The DNA/DOTAP was then aspirated from the flask and the cells were given 15 ml fresh culture medium. After a further 24 h, selection was initiated by removing the culture medium and adding selection medium (IMDM+5% dialysed FCS+1 mg/ml G418). The cells were cultured at 37° C. in 5% $CO_2$ and fresh selection medium was added as necessary. Culture supernatants were then tested by ELISA for the presence of antibody as described below.

Detection of Secreted Ab in Transfection Supernatants by ELISA:

Microtitre plates were coated with 50 μl/well anti-human IgFc (Sigma, catalogue number I-2136) in PBS at 2.5 μg/ml overnight at 4° C. The coating Ab was removed and the plates were blocked by addition of 100 μl/well blocking buffer (PBS +1% BSA +5% FCS +1% heat-inactivated normal rabbit serum (NRS)) overnight at 4° C. The transfection supernatants were added (50 μl/well) for at least 1h at room temperature. The wells were washed with PBS/0.5% TWEEN-20 (Polyoxyethylene-20-sorbitan monolaurate) (PBS/TWEEN). Biotinylated sheep anti-human Ig (Amersham, catalogue number RPN 1003) diluted 1/5000 in blocking buffer or biotinylated goat anti-human kappa light chain (Sigma, catalogue number B-1393) diluted 1/1000 in blocking buffer was added (50 μl/well) for 1h at room temperature. The wells were washed with PBS/TWEEN and 50 μl/well EXTRAVIDIN (modified egg protein)-peroxidase (Sigma, catalogue number E-2886) was added for 30 min at room temperature. The wells were washed once more and 100 μl/well of substrate o-phenylenediamine dihydrochloride (Sigma, catalogue number P-7288) was added. Colour change was measured at 492 nM using a MULTISKAN PLUS photometer microtitre plate reader.

Detection of Binding to Campath-1 Antigen by ELISA:

Microtitre plates were coated with 50 μl/well-anti-mouse Ig Fc (Sigma, catalogue number M-4280) in PBS at 2.5 μg/ml overnight at 4° C. The coating Ab was removed and the plates were blocked by addition of 100 μl/well blocking buffer (PBS+1% BSA+5% FCS+1% heat-inactivated NRS) overnight at 4° C. Purified recombinant Campath-1 Ag-fusion protein (sequence encoding the CD52 peptide backbone fused to sequence encoding mouse CH2 and-CH3 domains, and purified on a protein A column) was then added at 4 μg/ml to each well (50 μl/well) in PBS overnight at 4° C. The wells were then washed with PBS/Tween and the transfection supernatants were added (50 μl/well) for at least 1 h at room temperature. The wells were washed with PBS/Tween and biotinylated sheep anti-human Ig (Amersham, catalogue number RPN 1003) diluted 1/5000 in blocking buffer was added (50 μl/well) for 1 h at room temperature. The wells were washed with PBS/Tween and 50 μl/well ExtrAvidin-peroxidase (Sigma, catalogue number E-2886) was added for 30 min at room temperature. The wells were washed once more and 100 μl/well of substrate o-phenylenediamine dihydrochloride (Sigma, catalogue number P-7288) was added. Colour change was measured at 492 nM.

Assessment of Non-binding Mutants by ELISA:

"Wild-type" purified Campath-1H Ab binds strongly to recombinant Campath-1 Ag-fusion protein in ELISA assays. To provide a comparison for assessing non-cell-binding antibodies, the wild-type Ab can be titrated down in concentration until binding is just detectable. This may be referred to as "1 Ab binding unit". A suitable non-binding mutant of the wild-type will not show detectable binding at many times this concentration e.g. 100 times, or 1000 times, or preferably 10,000 times this concentration of wild-type Campath-1H Ab.

Assessment of Non-binding Mutants In Vivo:

An alternative method which can be applied to assess non-binding potential is described. Because we know that the wild-type Campath-1H Ab elicits a strong anti-immunoglobulin response in transgenic mice expressing human CD52 (see next section for details on these mice), purified deaggregated preparations of the mutants can be used in vivo to assess whether they are immunogenic. If an anti-globulin response cannot be detected at doses between 1 μg and 1 mg deaggregated mutant per mouse, this is a good indication that the mutant is unable to bind CD52.

B. In Vivo Models of Tolerance Induction:

To test the ability of the minimal mutants of Campath-1H to tolerize to the wild-type Campath-1H Ab in vivo, transgenic mice are used. For example, transgenic mice expressing human CD52 behind a murine CD2 promoter to mimic the expression of CD52 on T-cells can be used.

To create such mice, a 2.8 kb genomic fragment containing the 2 exons of the human CD52 gene as well as 4.5 kb upstream and 3' flanking sequence of the human CD2 gene can be introduced into the genome of transgenic mice. It is thought that strong control regions are present 3' to the human CD2 gene that determine the high levels and tissue-specific expression of the gene (Greaves et al, 1989). By this method, four CD52/CBA founders were established that transmitted the transgene. Indeed, when peripheral blood staining of their offspring was analysed by fluorescence activated cell sorting and 2-colour staining, it was shown that the cells expressing mouse CD3 (T-cells) also expressed human CD52 (D. Kioussis, unpublished data). These mice were bred to homozygosity and greater than 95% of their T-cells express high levels of human CD52 on the cell surface.

These mice produce a vigorous anti-globulin response (titre of 1/1000 or greater) to wild-type Campath-1H at doses of 1 to 10 mg/mouse. This anti-globulin response includes an anti-id component as the CDR loops are rat sequence. The effectiveness of the minimal mutants to tolerize to subsequent challenge of wild-type Campath-1H Ab may be assessed in the following ways:

1. Intravenous administration of a single dose (0.5 to 1 mg/mouse day 0) of each non-cell-binding mutant or irrelevant control Ab (deaggregated by ultracrentrifugation) followed by challenge with 1 to 10 mg wild-type Campath-1H Ab at 4 to 6 wks. Tail bleeds 10 days post challenge are tested by ELISA for Campath-1H anti-Id specificity.
2. Intravenous administration of multiple doses (0.5 to 1 mg/mouse) of deaggregated non-cell-binding mutant or control Ab over 2 months prior to challenge with 1 to 10 mg wild-type Campath-1H Ab. Tail bleeds 10 days post challenge are tested by ELISA for Campath-1H anti-id specificity. In both cases, the irrelevant control Ab is be an isotype-matched non-cell-binding Ab in mice such as Campath-9 which is a humanized anti-CD4 Ab (Gorman et al, 1991).

C. How the Strategy Could Be Adopted For Human Therapy:

An amount (e.g. 500 mg) of the non-cell-binding form of the therapeutic antibody would be administered to a patient awaiting treatment with the therapeutic antibody. Preferably the non-cell-binding antibody as administered is freshly deaggregated (for example by passage through a fine filter). A period of time later (for example 7 days), during which time the T-cells and B-cells would become tolerised, the wild-type form of the therapeutic antibody would be given.

1:). Additional considerations:

1. It should be easier to tolerize to a minimal mutant than to HGG or to mixed chain Ab molecules.

In the tolerance models of Benjamin et al (1986), tolerance to polyclonal HGG was induced in mice following depletion of CD4+ T-cells, but also using deaggregated material. It was found that tolerance to these soluble proteins could be achieved relatively easily. Also, in the work of Isaacs and Waldmann (1994), CD4 Ab were given during tolerance induction to the non-cell-binding mixed chain Ab molecules (irrelevant and antigen specific H- and L-chains), or non-cell-binding forms were used as tolerogens in their own right following their deaggregation.

In our modified approach to inducing tolerance using a minimal mutant, the foreigness of the protein will be less than that of polyclonal HGG or of the mixed chain Ab molecules in mice. In cases where the therapeutic mAb is humanized, only the CDR loops (and in some cases, some framework positions) are comprised of rodent sequence. It therefore may be possible to tolerize with a deaggregated minimal mutant in the absence of CD4 mAb. However, even if CD4 administration was required, a humanized therapeutic CD4 is available (CAMPATH-9; Gorman et al, 1991). The studies in transgenic animals should address these details.

2. Creation of a monovalent form of the minimal mutant (FIG. 4).

Thus far we have considered tolerance induction using a minimal mutant that is essentially like the wild-type therapeutic except for minimal residue change(s) that will disrupt antigen binding. We also propose a monovalent form that is also significantly smaller than the minimal mutant.

In one embodiment, the monovalent form is a single-chain Fv [formed by the VL, a short peptide linker (such as those reviewed in Huston et al, 1991) and the mutated VH] genetically fused with the sequence encoding the hinge-CH2-CH3 of human IgG1. This construct is expressed in association with a truncated heavy chain (hinge-CH2-CH3 only, Routledge et al, 1991) such that a protein is expressed that is composed essentially of a single Ab-combining site and a functional Ig Fc domain. The immunogenicity of the different peptide linkers is expected to be negligible given their small size (generally 14 to 18 residues in length) and abundance of small residues (eg Gly and Ser) making up the linkers. A popular choice is the 15-residue linker $(Gly_4Ser)_3$ in which the serine residues confer extra hydrophilicity on the peptide backbone (to inhibit its intercalation between the variable domains during folding) and which is otherwise free of side chains that might complicate domain folding (Huston et al, 1988).

SFv have been expressed in mammalian cells from a number of different antibodies and have been shown to fold into the correct conformation for antigen-binding by functional activity (Gilliland et al, 1996). The Fc portion is a preferred feature which should ensure serum half-life comparable to the minimal mutant and to the wild-type therapeutic Ab, whilst monovalency will ensure that binding to CD52 is greatly reduced due to the decrease in avidity. We have already shown from the CDR-swapping experiments (section A1) that the Campath-1 Ab binds poorly to CD52 in a monovalent form. In addition to reducing the avidity of the molecule, the smaller size may be a bonus: in classical tolerance experiments, it was found that the smaller the molecule, the better it was at inducing tolerance (Parish and Ada, 1969; Anderson, 1969; Miranda et al, 1973). By combining monovalency with a non-cell-binding mutant, a highly effective tolerogen may be obtained.

References

Anderson B. 1969. Induction of immunity and immunologic paralysis in mice against polyvinyl pyrrolidone. J Immunol 102, 1309-1313.

Benjamin R J, Cobbold S P. Clark M R and Waldmann H. 1986. Tolerance to rat monoclonal antibodies: implications for serotherapy. J Exp Med 163, 1539-1552.

Bird R E, Hardman K D, Joacobson J W. 1988. Single-chain antigen-binding proteins. Science 242, 423-426.

Brown J H, Jardetzky T S, Gorga J C, Stern", Urban R G, Strominger J L, Wiley D C. 1993. Three-dimensional structure of the human class II histocompatability antigen HLA-DR1. Nature 364, 33-39.

Chiller J M, Habicht G S, Weigle W O. 1971. Kinetic differences in unresponsiveness of thymus and bone marrow cells. Science 171, 813-815.

Chothia C and Lesk A M 1987. Canonical structures for the hypervariable regions of immunoglobulins. J Mol. Biol. 196, 901-917.

Chothia C, Lesk A M, Tramontano A, Levitt M, Smith-Gill S J. Air G, Sheriff S, Padlan E A, Davies D, Tulip W R, Colman P M, Spinelli S, Alzari P M, Poljak R J. 1989. Conformations of immunoglobulin hypervariable regions. Nature 342, 877-883.

Chothia C, Lesk A M, Gherardi E, Tomlinson I M, Walter G, Marks J D, Llewelyn, M 8, Winter G. 1992. Structural repertoire of the human VH segments. J Mol Biol 227, 799-817.

Cobbold S P. Clark M R. Benjamin R J, Waldmann H. Monoclonal antibodies and their use. EP 0 536 807 and EP 0 240 344. Wellcome Foundation Ltd.

Cunningham, B. C. and Wells, J. A. 1989. High resolution epitope mapping of hGH-receptor interactions by alanine-scanning mutagenesis. Science, 244, 1081-1085.

Gilliland L K, Norris N A, Marquardt H, Tsu T T. Hayden M S, Neubauer M G, Yelton D E. Mittler R S, Ledbetter J A. 1996. Rapid and reliable cloning of antibody variable regions and generation of recombinant single chain antibody fragments. Tissue Antigens, 47, 1-20.

Gorman S D, Clark M R, Routledge, E G, Cobbold S P, Waldmann H. 1991. Reshaping a therapeutic CD4 antibody. Proc Natl Acad Sci USA 88, 4181-4185.

Gram H, Marconi L A, Barbas C F 3rd, Collet T A, Lerner R A, Kang A S. 1992. In vitro selection and affinity maturation of antibodies from a naive combinatorial immunoglobulin library. Proc Natl Acad Sci USA 89, 3576-3580.

Greaves D R. Wilson F D, Lang G, Kioussis D. 1989. Human CD2 3'-flanking sequences confer high-level, T-cell specific, position-independent gene expression in transgenic mice. Cell 56, 979-986.

Hale G, Xia M-Q, Tighe H P, Dyer M J S, Waldmann H. 1990. The CAMPATH-1 antigen (CDw52). Tissue Antigens 35, 118-127.

Hale G, Hoang T, Prospero T, Watt S M, Waldmann H. 1983. Removal of T cells from bone marrow for transplantation: comparison of rat mono-clonal anti-lymphocyte antibodies of different isotypes. Mol Biol Med 1, 305-319.

Huston J S, Mudgett-Hunter M, Tai M-S, McCartney J, Warren F. Haber E, Oppermann H. 1991. Protein engineering of single-chain Fv analogs and fusion proteins. Methods Enzymol 203, 46-88.

Hoogenboom H R, Griffiths A D, Johnson K S, Chiswell D J, Hudson P, Winter G. 1991. Multi-subunit proteins on the surface of filamentous phage: methodologies for displaying antibody (Fab) heavy and light chains. Nucl Acids Res 19, 4133-4137.

Hunt D F, Michel H, Dickinson T A, Shabanowitz J, Cox A L, Sakaguchi K, Apella E, Grey H M, Sette A. 1992. Peptides presented to the immune system by the murine class II major histocompatability molecule I-Ad. Science 256, 1817-1820.

Huston J S, Levinson D, Mudgett-Hunter M et al. 1988. Protein engineering of antibody binding sites: recovery of specific activity in an anti-digoxin single-chain Fv analogue produced in Escherichia coli. Proc Natl Acad Sci USA, 85, 5879-5883.

Isaacs J D, Watts R A, Hazleman B L et al. 1992. Humanized monoclonal antibody therapy for rheumatoid arthritis. Lancet 340, 748-752.

Isaacs J D, Waldmann H. 1994. Helplessness as a strategy for avoiding antiglobulin responses to therapeutic monoclonal antibodies. Therapeutic Immunol 1, 303-312.

Jones P T, Dear P H, Foote J, Neuberger M S, Winter G. 1986. Replacing the complementarity-determining regions in a human antibody with those from a mouse. Nature 321, 522-525.

Kabat E A, Wu T T, Reid-Miller M, Perry H M, Gottesman K S. 1987. Sequences of Proteins of Immunological Interest, 4th ed. Washington DC, Public Health Service, NIH.

Levitskaya J, Coram M, Levitsky V, Imreh S, Steigerwald-Mullen P M, Klein G, Kurilla M G, Masucci M G. 1995. Inhibition of antigen processing by the internal repeat region of the Epstein-Barr virus nuclear antigen-1. Nature 375, 685-488.

Lockwood C M, Thiru S, Isaacs J D, Hale G, Waldmann H. 1993. Long-term remission of intractable systemic vasculitis with monoclonal antibody therapy. Lancet 341, 1620-1622.

Low N M, Hollinger P H, Winter G. 1996. Mimicking somatic hypermutation: affinity maturation of antibodies displayed on bacteriophage using a bacterial mutator strain. J Mol Biol 260, 359-368.

Miranda J J Zola H, Howard J G. 1973. Studies on immunological paralysis. X. Cellular characteristics of the induction and loss of tolerance to leva (polyfructose). Immunology 23, 843-855.

Novotny J, Bruccoleri R E, Newell J, Murphy D, Haber E, Karplus M. 1983. Molecular anatomy of the antibody binding site. J Biol Chem 258, 14433-14437.

Page M J. Sydenham M A. 1991. High level expression of the humanized monoclonal antibody Campath-1H in Chinese hamster ovary cells. Biotechnol. 9, 64-68.

Parish C R, Ada G L. 1969. The tolerance inducing properties in rats of bacterial flagellin cleaved at the methionine residues. Immunology 17, 153-164.

Riechmann L, Clark M, Waldmann H, H, Winter G. 1988. Reshaping human antibodies for therapy. Nature 332, 323-327.

Routedge E G, Gorman S D, Clark M R. 1993. Reshaping antibodies for therapy. In Protein Engineering of Antibody Molecules for Prophylactic and Therapeutic Applications in Man. ed. M Clark, Academic Titles, Nottingham, UK. pp 13-44.

Routedge E G, Lloyd I, Gorman S D, Clark M, Waldmann H. 1991. A humanized monovalent CD3 antibody which can activate homologous complement. Eur J Immunol 21, 2717-2725.

Rudensky A Y, Preston-Hurlburt P, Hong S, Barlow A, Janeway C A Jr. 1991. Sequence analysis of peptides bound to MHC class II molecules. Nature 353, 622-627.

Rudensky A, Janeway C A Jr. 1993. Studies on Naturally processed peptides associated with MHC class II molecules. In Sette A (ed.) Naturally Processed Peptides. Basel, Karger, pp 134-151.

Xia M-Q Tone M, Packman L. Hale G, Waldmann H. 1991. Characterization of the CAMPATH-1 (CDw52) antigen: biochemical analysis and cDNA cloning reveal an unusually small peptide backbone. Eur J Immunol 21, 1677-1684.

The invention claimed is:

1. A method of improving treatment of a condition associated with CD52 expression in a patient, wherein the condition is treated by administering a CD52-binding therapeutic antibody to the patient, wherein the improvement comprises:
   administering to the patient a single variant antibody of said CD52-binding therapeutic antibody,
   wherein the single variant antibody differs in amino acid sequence at one or two amino acid residues as compared to the amino acid sequence of said CD52-binding therapeutic antibody and the one or two amino acid residues are in a complementary determining region (CDR) involved in CD52 binding,
   wherein the single variant antibody has CD52-binding-affinity reduced to 50% or less as compared to said CD52-binding therapeutic antibody,
   wherein the single variant antibody induces partial immunological tolerance to said CD52-binding therapeutic antibody, and
   wherein the variant antibody shows detectable binding to CD52 in an ELISA at 10,000 times the minimum concentration at which binding of the therapeutic antibody is detectable,
   thereby improving treatment of a condition associated with CD52 expression by reducing the antiglobulin response directed against said CD52-binding therapeutic antibody upon subsequent administration of said CD52-binding therapeutic antibody to the patient.

2. The method according to claim 1, wherein the one or two amino acid residue(s) that differ from the therapeutic antibody is/are identified using one or more techniques selected from the group consisting of X-ray crystallography, computer modeling, comparative modeling, CDR swapping, Alanine scanning, phage display and cycling of V-region genes.

3. The method according to claim 1, wherein the one or two amino acid residue(s) is/are modified by genetic manipulation.

4. The method according to claim 3, wherein the genetic manipulation is site-directed mutagenesis.

5. The method according to claim 1, wherein the affinity for antigen binding of the variant antibody is reduced to 10% or less as compared to the therapeutic antibody, but shows detectable binding to CD52 in an ELISA at 10,000 times the minimum concentration at which binding of the therapeutic antibody is detectable.

6. The method according to claim 5, wherein the affinity for antigen binding of the variant antibody is reduced to 1% or less as compared to the therapeutic antibody, but shows detectable binding to CD52 in an ELISA at 10,000 times the minimum concentration at which binding of the therapeutic antibody is detectable.

7. The method according to claim 1, text "wherein the one or two differences in a CDR of the variant antibody as compared to the therapeutic antibody are located in VH CDR2".

8. The method according to claim 1, wherein the difference is a single or a double amino acid substitution.

9. The method according to claim 8, wherein the single or double amino acid substitution is located in VH CDR2.

10. The method according to claim 1, wherein the therapeutic antibody is a humanized antibody.

11. The method according to claim 1, wherein each of the one or two different amino acid residue(s) reduces the affinity for CD52 binding of the variant antibody.

12. The method according to claim 1, wherein the affinity for CD52 binding of the variant antibody is reduced such that the antibody does not show detectable binding to CD52 in an ELISA at 100 times the minimum concentration at which binding of the therapeutic antibody is detectable, but shows detectable binding to CD52 in an ELISA at 10,000 times the minimum concentration at which binding of the therapeutic antibody is detectable.

13. The method according to claim 12, wherein the variant antibody does not show detectable binding to CD52 in an ELISA at 1,000 times the minimum concentration at which binding of the therapeutic antibody is detectable, but shows detectable binding to CD52 in an ELISA at 10,000 times the minimum concentration at which binding of the therapeutic antibody is detectable.

* * * * *